US011376351B2

(12) United States Patent
Guthrie et al.

(10) Patent No.: US 11,376,351 B2
(45) Date of Patent: Jul. 5, 2022

(54) SMART BREAST PUMP SYSTEM

(71) Applicant: Moxxly, LLC, Wilmington, DE (US)

(72) Inventors: Gabrielle V. Guthrie, San Francisco, CA (US); Santhi Analytis, San Francisco, CA (US); Cara C. Delzer, San Francisco, CA (US)

(73) Assignee: Moxxly, LLC, Wilmington, DE (US)

( * ) Notice: Subject to any disclaimer, the term of this patent is extended or adjusted under 35 U.S.C. 154(b) by 96 days.

(21) Appl. No.: 14/859,265

(22) Filed: Sep. 19, 2015

(65) Prior Publication Data

US 2016/0082166 A1   Mar. 24, 2016

Related U.S. Application Data

(60) Provisional application No. 62/053,079, filed on Sep. 19, 2014.

(51) Int. Cl.
*A61M 1/06* (2006.01)

(52) U.S. Cl.
CPC .............. *A61M 1/062* (2014.02); *A61M 1/06* (2013.01); *A61M 2205/3334* (2013.01); *A61M 2205/3337* (2013.01); *A61M 2205/3379* (2013.01); *A61M 2205/3569* (2013.01); *A61M 2205/3584* (2013.01); *A61M 2205/502* (2013.01); *A61M 2205/702* (2013.01)

(58) Field of Classification Search
CPC .......................... A61M 1/06; A01J 5/007–0138
See application file for complete search history.

(56) References Cited

U.S. PATENT DOCUMENTS

| 5,843,029 A * | 12/1998 | Bachman | A61M 1/064 604/74 |
|---|---|---|---|
| 6,427,871 B1 * | 8/2002 | Suero | B67D 1/1206 222/36 |
| 6,440,100 B1 | 8/2002 | Prentiss | |
| 6,872,200 B2 * | 3/2005 | Mann | A61M 5/14244 604/890.1 |
| 2004/0210405 A1 * | 10/2004 | Mogadam | B67D 3/0054 702/50 |
| 2007/0060873 A1 * | 3/2007 | Hiraoka | A61M 1/0066 604/74 |
| 2010/0130936 A1 * | 5/2010 | Voss | A61M 25/0017 604/158 |

(Continued)

OTHER PUBLICATIONS

Jacqueline C. Kent et al., Importance of Vacuum in Breast Milk Expression; Breastfeeding Medicine, vol. 3, No. 1, Mar. 2008, pp. 11-19; New Rochelle, New York, USA.

(Continued)

*Primary Examiner* — Scott J Medway
*Assistant Examiner* — John A Doubrava
(74) *Attorney, Agent, or Firm* — Loyal IP Law, PLLC; Travis Banta

(57) ABSTRACT

This disclosure generally relates to a smart breast pump system that includes at least one sensor to monitor the expression of breast milk. The smart breast pump system may further include a mobile device which wirelessly receives sensor data from the at least one sensor. Additionally, the smart breast pump system may further include at least one server device, which wirelessly receives sensor data from the at least one mobile device.

18 Claims, 5 Drawing Sheets

(56) References Cited

U.S. PATENT DOCUMENTS

2014/0257206 A1* 9/2014 Fateh ................... A61F 9/0026
604/290
2014/0288466 A1 9/2014 Alvarez et al.
2015/0283311 A1* 10/2015 Alvarez ............... A61M 1/066
604/74

OTHER PUBLICATIONS

Donna T. Ramsay et al., Milk Flow Rates Can Be Used to Identify and Investigate Milk Ejection in Women Expressing Breast Milk Using an Electric Breast Pump; Breastfeeding Medicine, vol. 1, No. 1, Mar. 2006, pp. 14-23, New Rochelle, New York, USA.

* cited by examiner

SMART BREAST PUMP SYSTEM

BACKGROUND

1. Technical Field

This disclosure relates generally to a smart breast pump system. More specifically, the smart breast pump system disclosed herein relates to a system that provides women a discrete low profile breast pump that may be worn underneath regular clothing which also monitors and tracks a woman's milk production and supply.

2. Description of the Related Art

Upon the birth of a child, one of the first natural instincts of a new mother is to feed the new baby by nursing. Many new mothers describe their first nursing experience with a new baby as forming an unbreakable emotional bond between the new baby and the new mother. Accordingly, nursing can be a tremendously emotional experience for women who give birth to new babies. Unfortunately, many women experience difficulty in nursing infants, for a variety of reasons. This difficulty may leave some women feeling inadequate, depressed, and otherwise distraught about their inability to participate in a natural process of nursing a new infant. Further, a crying hungry infant only exacerbates its mother's emotional condition and feelings of inadequacy in being unable to feed her baby.

Many solutions have been proposed for solving a mother's inability to express milk in sufficient quantity to provide adequate nourishment for a baby. Supplements, such as baby formula, have been developed as an alternative source of food for a baby, thereby reducing or eliminating the need for a mother to nurse her baby. However, most medical experts currently agree that breast milk is superior to manufactured supplements. Thus, supplements are a non-ideal choice for overcoming nursing difficulties. Another solution to increase a woman's breast milk production has been the advent of a breast pump. Conventional breast pumps require a woman to completely or nearly completely remove all clothing covering her breasts in order to attach the pump to a breast. Some breast pumps require that a woman hold the pump to her breast while it suctions milk from the breast. Other breast pumps are implemented by harnesses that contort a woman's breast into a position suitable to create suction between the pump and the breast to produce milk. Further, in order to use a harness, a woman must remove her shirt and undergarments each time she intends to use a breast pump, making the use of the harness not only uncomfortable, but also inconvenient. Many of these breast pumps are so difficult to use, painful to the woman, and so intrusive on the woman's other obligations, that even though breast milk is produced, a woman may still emotionally traumatized by the breast pumping experience.

Further, many women who are not available to feed an infant during certain periods of the day may use a breast pump to pump milk to store and use to feed an infant at a later time. However, while mandated by law in some cases, many places lack a convenient or discrete place to allow a woman to operate a breast pump. Thus, lactating women are relegated to empty offices, bathroom stalls, empty conference rooms, or other makeshift areas in which women can discretely pump milk to store for an infant's later use. Moreover, because conventional breast pumps have been so difficult to use, many women experience significant inconvenience in their daily schedules and devote a substantial portion of a work day to operating the breast pump. While many employers, for example, accommodate women and their need to pump, the women themselves find that pumping makes them less productive and interrupts progress they are making on other projects.

Accordingly, it is one object of this disclosure to provide a simple to use smart breast pump system. It is another object of this disclosure to provide a smart breast pump system that may be continuously worn as a low profile discrete pump system. It is another object of this disclosure to reduce the emotional toll pumping takes on a woman by monitoring milk expression and tracking an amount of breast milk stored for future use.

It is a further object of this disclosure to provide a mobile device that provides wireless control over the smart breast pump system. Yet another object of this disclosure is to transmit information collected by remote device to a remote server for access by other concerned parties, such as another parent or guardian of the child for whom the woman is pumping milk.

SUMMARY

Disclosed herein is a smart breast pump system. In one embodiment, the smart breast pump system comprises at least one sensor to monitor the expression of breast milk. The smart breast pump system may further include a mobile device which wirelessly receives sensor data from the at least one sensor.

Also disclosed herein is a smart breast pump system, which comprises at least one sensor to monitor the expression of breast milk. The smart breast pump system may further include a mobile device which wirelessly receives sensor data from the at least one sensor. Further, the smart breast pump system may further include at least one server device, wirelessly receiving the sensor data from the at least one mobile device.

BRIEF DESCRIPTION OF THE DRAWINGS

The accompanying drawings illustrate an embodiment of a smart breast pump system.

DETAILED DESCRIPTION OF PREFERRED EMBODIMENTS

In the following description, for purposes of explanation and not limitation, specific techniques and embodiments are set forth, such as particular techniques and configurations, in order to provide a thorough understanding of the device disclosed herein. While the techniques and embodiments will primarily be described in context with the accompanying drawings, those skilled in the art will further appreciate that the techniques and embodiments may also be practiced in other similar devices.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to particular embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Figure 1:
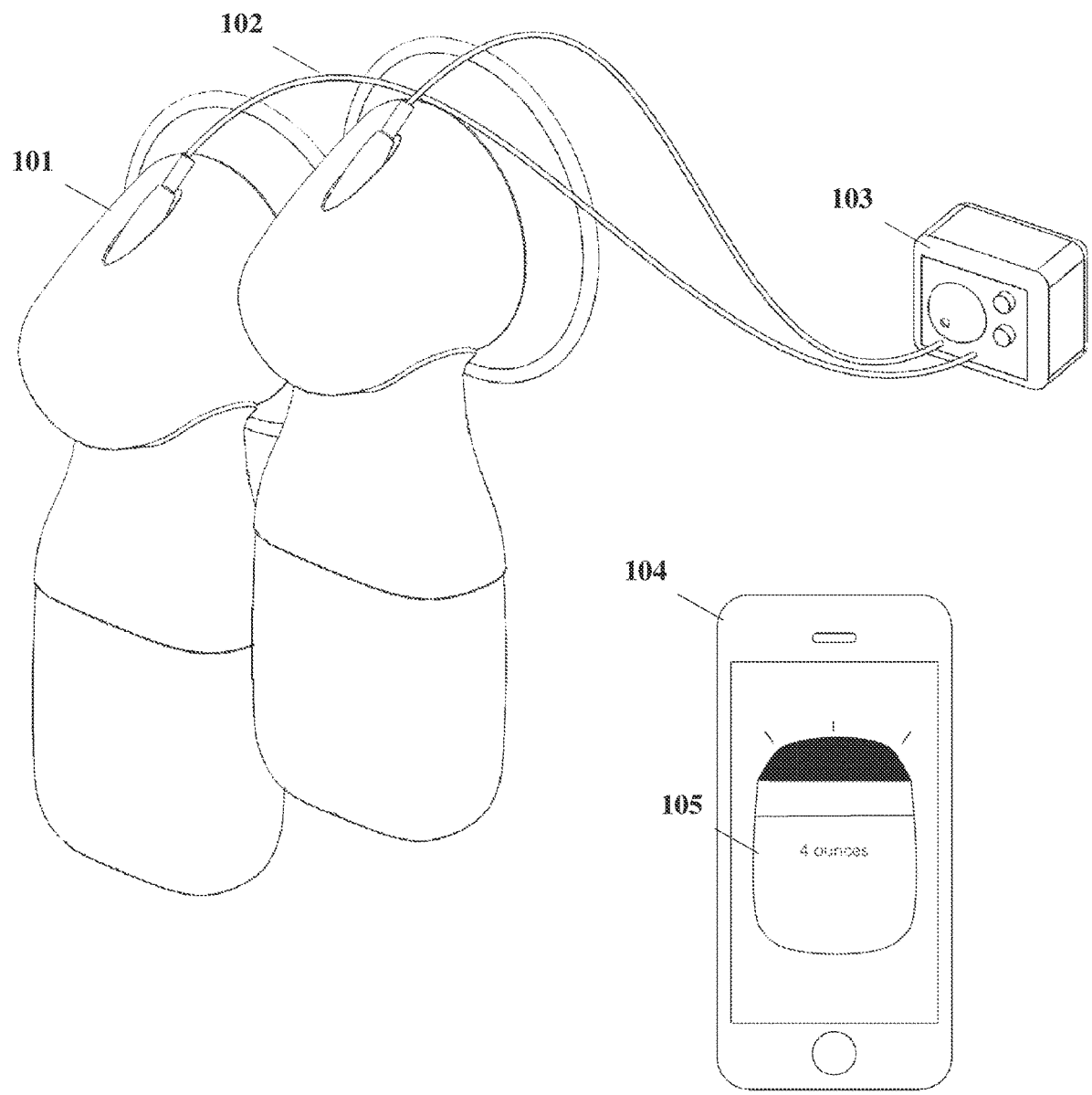
FIG. 1 illustrates an exemplary smart breast pump system.

FIG. 1 illustrates an exemplary smart breast pump system. The smart breast pump system includes a milk capture and collection element 101. Milk capture and collection element 101 includes a cup portion that substantially matches the curve of a woman's breast. The cup portions may be interchangeable and replaceable to accommodate various different sized breasts, areolas, and nipples or may be configured in a "one size fits all" fashion. Preferably, however, women with larger areola and nipple regions may choose to use a cup portion with a larger diameter while women with smaller areola and nipple regions may choose to use a cup portion with a smaller diameter cup portion. Because an appropriately sized cup portion increases the degree of contact between the woman's breast and the cup portion, the cup portion is more comfortable for a woman to wear while at the same time creating a more substantial air tight seal between the woman's breast and the cup portion. The cup portion is naturally centered over a woman's nipples as the cup portion is applied by the woman to her breast. Further because the cup portions substantially match the curve of the woman's breast, milk capture and collection element 101 is comfortable for a woman to wear which results in reduced pain, reduced anxiety, reduced stress, and a more emotionally satisfying experience than conventional pumping systems. Accordingly, breast pumping with the smart breast pump system disclosed herein provides a more natural massaging sensation to a woman, further reducing anxiety and stress with the breast pumping experience.

Cup portions may range from approximately 3 to 5 inches in diameter and are less than approximately one centimeter in thickness. The cup portion may advantageously be held to a woman's breasts by a standard nursing bra. Given the relative small size of a particular cup portion, milk capture and collection element 101 may be persistently and comfortably held in place by a nursing bra for a substantial period of time. Because milk capture and collection element 101 may be worn for a substantial period of time, such as an entire work day, a woman may pump her breasts at any time without disrobing and, therefore, without needing to find a private place to pump.

Cup portions may attach to a pump portion of milk capture and collection element 101. A pump portion of milk capture and collection element 101 comprises a vacuum pump and a vacuum chamber through which milk can flow uninterrupted as it is expressed into a milk collection portion of milk capture and collection element 101, which will be discussed in detail below. The pump portion of milk capture and collection element 101 may be implemented as a single unit or may be implemented as, for example, an external vacuum pump configured to apply vacuum pressure to a woman's breast via the vacuum chamber. The pump portion of the milk capture and collection element 101 receives a funnel end of the cup portions and attaches, using, for example, a friction based connection, the cup portion to the pump portion. Other types of connections between various portions of milk capture and collection element 101 may include snaps, quick connects, or twist (threaded) attachments. Milk capture and collection element 101 may be substantially leak-proof. For example, connections between various portions of milk capture and collection element 101 may prevent milk leaks. Accordingly, the cup portions funnel milk into the pump portion as it pumped from a woman's breast. The pump portion allows the milk to drain into a milk collection portion of milk capture and collection element 101. The milk collection portion will be discussed in further detail below, particularly with respect to FIG. 3A and FIG. 3B.

Milk capture and collection element 101 may further include a sensor portion for detecting and measuring an amount of milk expressed during a particular breast pumping session. The sensor portion may include sensors that rely on optical, electrical, or mechanical drop by drop counting, including Hall Effect sensors, phototransistors, force sensors, or capacitive liquid level sensing to detect an amount of milk that has been collected during a breast pumping session. In one embodiment, sensors may begin to operate when other portions of milk capture and collection element 101 are installed. For example, a sensor may be triggered to begin operation when the cup portion of a milk capture and collection element 101 is installed on a pump portion of the milk capture and collection element 101. Alternatively, a sensor may be triggered to begin operation when the milk collection portion of the milk capture and collection element 101 is installed on the pump portion of the milk capture device. Alternatively, a sensor may be triggered to begin operation based on a magnetic sensor sensing one or more magnets placed within cup portion of milk capture and collection element 101 or within the milk collection portion of the milk capture and collection element 101. Other technologies for triggering the sensor to begin operation include push button switches, snap domes, proximity sensors, pressure sensors, and other similar techniques known in the art. The milk capture and collection element 101 may provide a visual cue to the operator that the sensors have begun operation and are ready to measure data directly, or via mobile device 104, as discussed below. The sensor portion may have access to power from a battery contained within milk capture and collection element 101, include a microprocessor, and include a memory device in order to store data derived over up to ten pumping sessions with a duration averaging approximately 30 minutes per session. Data stored within a memory device may include, for example, a real-time flow rate in ounces per minute gathered every 5 seconds and total volume of milk pumped per pumping session.

Milk capture and collection element 101 connects via pneumatic tubing 102 to an external vacuum pump 103, in one embodiment. In this embodiment, external vacuum pump 103 may operate by either battery power or by alternating current ("AC") power supplied through a standard electrical outlet. External vacuum pump 103 creates vacuum pressure within the pump portion of milk capture and collection element 101 by drawing air away from the pump portion of milk capture and collection element 101.

The pump portion of milk capture and collection element 101 directs the vacuum pressure through the cup portion of milk capture and collection element 101 where the vacuum pressure is applied to a woman's breast. As vacuum pressure is applied to the woman's breast, an air-tight seal is formed between the cup portion of milk capture and collection element 101 and the skin on the woman's breast. Once the air-tight seal has been created, vacuum pressure is applied to a nipple on the woman's breast, causing the breast to express milk through the nipple. As shown in FIG. 1, pneumatic tubing 102 may connect to the milk capture and collection element 101 in a manner that allows milk to flow through the vacuum chamber of the pump portion of milk capture and collection element 101 without drawing milk into pneumatic tubing 102. In this embodiment, milk is allowed to flow freely from the nipple, through the vacuum chamber of the pump portion of milk capture and collection element 101 and into the milk collection portion of milk capture and collection element 101.

In another embodiment, a vacuum pump similar to external vacuum pump 103 may be disposed within the pump portion of milk capture and collection element 101. Accordingly, a battery may be included within the vacuum pump such that the vacuum pump has sufficient power to create enough vacuum pressure to cause a breast to express milk. A vacuum pump disposed within the pump portion of milk capture and collection element 101 may be disposed in such a manner as to allow the vacuum pump to apply vacuum pressure to a woman's breast, while simultaneously allowing milk to flow into the milk collection portion of milk capture and collection element 101. Regardless, a vacuum pump used in conjunction with the smart breast pump system disclosed herein are relatively small and substantially silent.

Each portion of the milk capture and collection element 101 that is exposed to either the user's skin or to milk is constructed using a flexible, soft, medical and food grade silicone. For example, medical grade silicone may be used to construct portions of milk capture and collection element 101 that may come into contact with the user's skin while food grade silicone may be used to construct portions of milk capture and collection element 101 that come into contact with milk. Each portion of the milk capture and collection element 101 may be independently sanitized and may also be constructed in a way to facilitate washing by automatic dishwasher.

Because the milk capture and collection element 101 is designed to maintain a low profile and fit discretely under a woman's clothes, a woman may not be able to easily interact with the milk capture and collection element 101. For example, since any user interface elements of the milk capture and collection element 101 would be covered by the woman's clothes, the woman many not be able to conveniently access milk capture and collection element 101 or receive information from milk capture and collection element 101 during use. Accordingly, mobile device 104 may be provided in the smart breast pump system as a solution to provide both control of the milk capture and collection element 101 and information from milk capture and collection element 101.

For example, mobile device 104 may be implemented as a smart phone, a tablet, a laptop computer, a desktop computer, a music storage and playback device, a personal digital assistant, or any other device capable of implementing a software application that may interact with, control, and provide information from milk capture and collection element 101. These exemplary devices may include a combination of one or more application programs and one or more hardware components. For example, application programs may include software modules, sequences of instructions, routines, data structures, display interfaces, and other types of structures that execute operation. Further, hardware components implementing modules and other means disclosed herein may include a combination of processors, microcontrollers, busses, volatile and non-volatile memory devices, non-transitory computer readable memory device and media, data processors, control devices, transmitters, receivers, antennas, transceivers, input devices, output devices, network interface devices, and other types of components that are apparent to those skilled in the art. While examples herein use a smart phone as an exemplary mobile device for controlling, interacting with, and receiving information from milk capture and collection element 101, any device capable of executing an application program may be similarly used in place of a smart phone.

Mobile device 104 may interface with a sensor portion of milk capture and collection element 101 using, for example, a Bluetooth low energy radio connection. Accordingly, mobile device 104 may receive information in real-time from a sensor within the sensor portion of milk capture and collection element 101, such as whether or not milk is flowing, how much milk has been collected during a particular pumping session, and the duration of a pump session. Further, mobile device 104 may interface with external vacuum pump 103 or a pump disposed within milk capture and collection element 101 to turn the pump on or off or otherwise control a pumping session. As information is received from the sensors in the sensor portion of milk capture and collection element 101, the data may be viewed in real-time via user interface 105 of mobile device 104. As shown in FIG. 1, user interface 105 shows that a woman has pumped four ounces of milk during a pumping session. Data displayed on user interface 105 of mobile device 104 may be updated in real-time, for example, by updating the interface every second. In one embodiment, a sensor within the sensor portion of milk capture and collection element 101 may detect new data every ten milliseconds which may be transmitted to/received by mobile device 104. Mobile device 104 may aggregate and use this data to update user interface 105 every second. A woman may use this information to determine whether or not she has completed pumping, should continue pumping, or should discontinue pumping.

A software application operating on mobile device 104 may provide further analysis. For example, mobile device 104 may calculate a volume of milk pumped per session, session times, session durations, pumping trends over time, and milk inventory information (i.e., milk that has been pumped and frozen, refrigerated, fed to a baby, or disposed of). Mobile device 104 may provide suggestions regarding pumping strategies. For example, mobile device 104 may suggest pumping at a certain time of day, suggest pumping for a certain duration of time, or suggest actions to take regarding milk inventory (i.e., freeze, refrigerate, feed to the baby, dispose, donate). In another example, mobile device 104 may receive information from the sensor portion of milk capture and collection element 101 passively. In other words, mobile device 104 may receive information from the sensor portion of milk capture and collection element 101 whether or not the software application is actively executing on the mobile device.

Figure 2A:
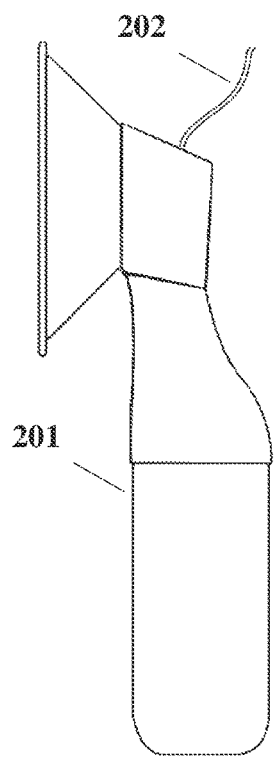
FIG. 2A illustrates a side view of an exemplary discrete breast pump element of the smart breast pump system.

FIG. 2A illustrates a side view of an exemplary discrete breast pump element of the smart breast pump system. In one embodiment, the exemplary discrete breast pump element of the smart breast pump system comprises a milk capture and collection element 201, similar to milk capture and collection element 101, shown in FIG. 1. In this embodiment, milk capture and collection element 201 includes a pneumatic tube 202 which is connected to an external vacuum pump, such as external vacuum pump 103, shown in FIG. 1. In this example, the smart breast pump system may forgo a sensor in the smart breast pump system and instead implement external vacuum pump 103 which may be controlled by mobile device 104, shown in FIG. 1. Accordingly, smart breast pump system may be used with or without a sensor in combination with a vacuum pump that may send data to and receive data from mobile device 104, shown in FIG. 1.

Figure 2B:
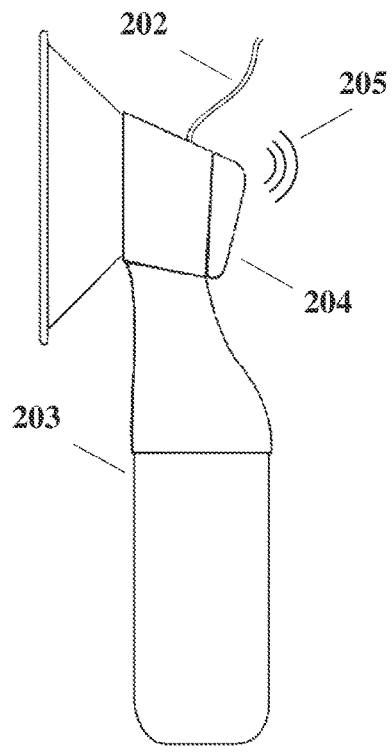
FIG. 2B illustrates a side view of an alternate embodiment of the exemplary discrete breast pump element of the smart breast pump system.

FIG. 2B illustrates a side view of an alternate embodiment of the discrete breast pump element of the smart breast pump system shown in FIG. 2A. In this embodiment, the discrete breast pump element of the smart breast pump system comprises a milk capture and collection element 203 and a pneumatic tube 202, as shown in FIG. 2A. However, in the embodiment of the milk capture and collection element 203 shown in FIG. 2B, milk capture and collection element 203 includes a smart sensor 204 which includes wireless communication circuitry 205 to communicate with, for example, mobile device 104, shown in FIG. 1. Smart sensor 204 operates similarly to the sensor portion of milk capture and collection element 101, discussed above with respect to FIG. 1. Essentially, smart sensor 204 includes a sensor for monitoring milk production and communicates milk production information via wireless communication circuitry 205 within smart sensor 204 to, for example, mobile device 104, shown in FIG. 1. Smart sensor 204 may further receive control instructions via wireless communication circuitry 205 from, for example, mobile device 104 shown in FIG. 1, that asserts control over milk capture and collection element 203. Smart sensor 204 may further communicate with an external vacuum pump directly or via a mobile device, such as mobile device 104 shown in FIG. 1, to create a closed feedback loop in which pump settings can be adjusted based on a woman's milk expression in real-time.

Figure 2C:
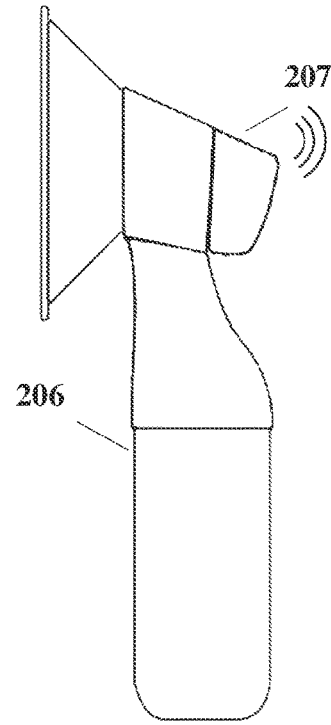
FIG. 2C illustrates a side view of a second alternate embodiment of the exemplary discrete breast pump element of the smart breast pump system.

FIG. 2C illustrates a side view of an alternate embodiment of the exemplary discrete breast pump element of the smart breast pump system. In this embodiment, the discrete breast pump element of the smart breast pump system comprises a milk capture and collection element 206 which is similar to milk capture and collection elements 201 shown in FIG. 2A, 203 shown in FIG. 2B, and 101 shown in FIG. 1. However, in this embodiment, milk capture and collection element 206 includes an integral smart sensor and internal pump 207. A smart sensor portion of smart sensor and internal pump 207 operates in a fashion similar to that described above with respect to smart sensor 204 shown in FIG. 2B and sensor portion of milk capture and collection element 101 shown in FIG. 1. In FIG. 2C, however, smart sensor and internal pump 207 includes a vacuum pump portion that is integral to milk capture and collection element 206. Here, again, smart sensor and internal pump 207 may further communicate directly or via a mobile device, such as mobile device 104 shown in FIG. 1, to create a closed feedback loop in which pump settings can be adjusted based on a woman's milk expression in real-time.

Figure 3A:
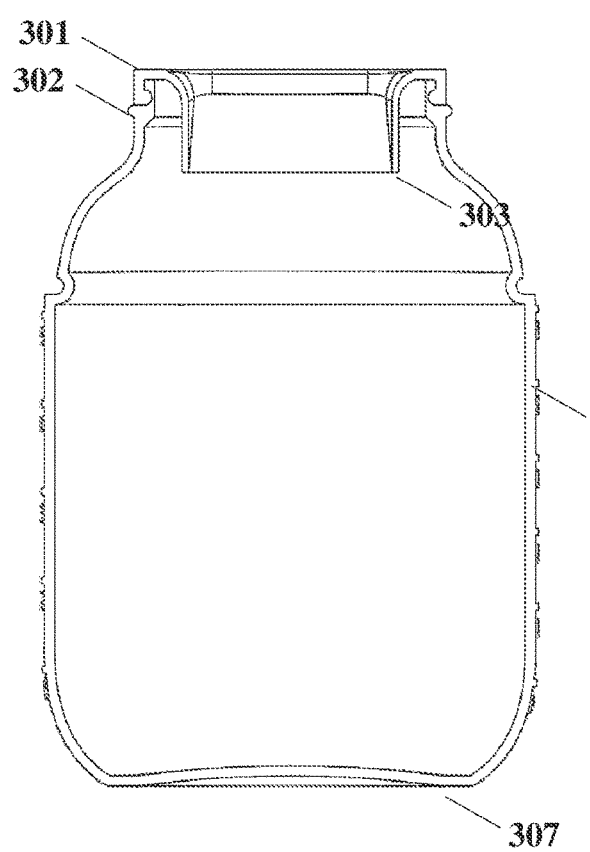
FIG. 3A illustrates a cross-sectional front view of a milk collection element of the smart breast pump system.

FIG. 3A illustrates a cross-sectional front view of a milk collection element of the smart breast pump system. The milk collection element shown in FIG. 3A comprises a valve 301 which can be inserted into bottle 304 and mate in a leak proof fashion with a stop 302 to ensure that valve 301 attaches firmly to bottle 304. Valve 301 may be implemented as a duckbill valve, a check valve, or any other one-way valve known in the art. Valve 301 further includes valve leaflets 303 that prevent the bottle from leaking or spilling whether the bottle 304 is currently in use or not. Valve leaflets 303 are configured to open and close as either an internal or external vacuum pump, such as vacuum pump 103 shown in FIG. 1, cycles during regular use. Accordingly, while suction is present during a pump cycle, valve leaflets 303 close. While suction is not present (or reduced) during a pump cycle, valve leaflets 303 open to allow milk to flow into bottle 304. While only a single pair of valve leaflets 303 are shown, multiple pairs of leaflets can be employed within the milk collection element of the smart breast pump system shown in FIG. 3A. For example, two pairs of valve leaflets 303 may be implemented side by side of each other in a manner such that valve 301 is pliable enough to allow for opening and closing as a vacuum pump cycles. Any number of valve leaflets 303 may be implemented to suit any particular desired implementation.

In one embodiment, the milk collection element shown in FIG. 3A may correspond to the milk collection portion of milk capture and collection element 101, discussed above. Accordingly, the milk collection element shown in FIG. 3A may attach to milk capture and collection element 101 in a manner that is substantially leak proof. The milk collection element shown in FIG. 3A further receives and collects milk as milk is pumped from a woman's breast. Advantageously, valve 301 is removable which allows a rubber nipple to be attached to bottle 304 for feeding a baby. Bottle 304 fits discretely under a woman's clothing and may collect between 3 and 8 ounces of milk. In the case where two milk capture and collection elements 101 are employed, one attached to each breast, the smart breast pump system is capable of collecting between 6 and 16 ounces of milk total before bottle or bottles 304 must be drained or replaced. Bottle 304 further includes a flat base 307 to allow bottle 304 to stably stand whether or not it contains milk, ensuring that bottle 304 does not tip or spill milk that has been collected.

Figure 3B:
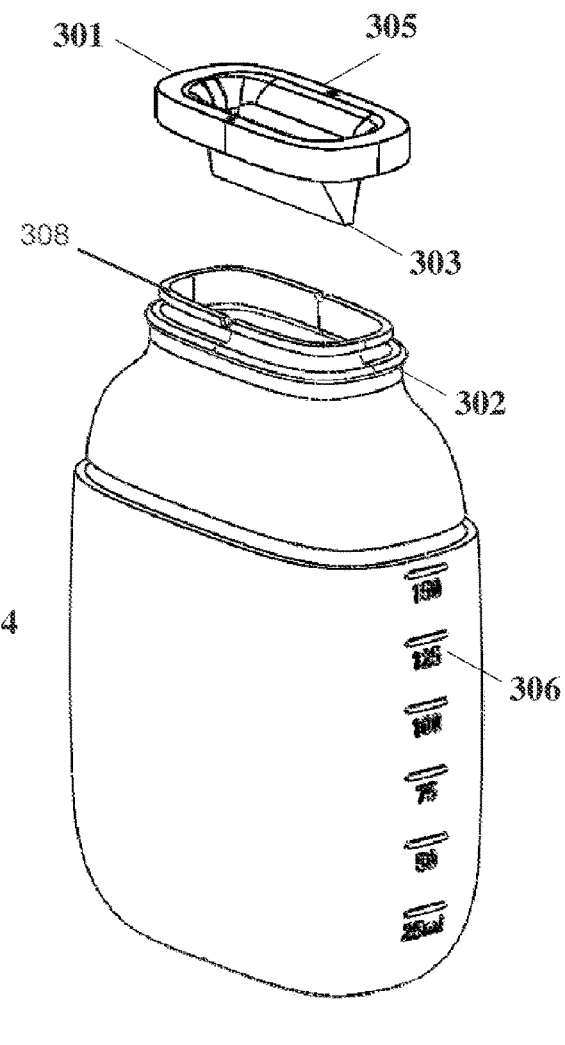
FIG. 3B illustrates a perspective view of the milk collection element including a one-way valve and a milk collection bottle.

FIG. 3B illustrates a perspective view of the milk collection element including a one-way valve and a milk collection bottle. The milk collection element shown in FIG. 3B is similar to the milk collection element shown in FIG. 3A, although from a different perspective. The milk collection element shown in FIG. 3B, like the milk collection element shown in FIG. 3A, includes a valve 301, a rim 308, a stop 302, and one or more pairs of valve leaflets 303. The milk collection element shown in FIG. 3B includes a sloped region 305 disposed within valve 301 to direct milk through valve 301 without catching and drying on the inside surface of valve 301. The milk collection element shown in FIG. 3B may further include indicia 306 of fluid levels. In this example, indicia 306 represents a graduated scale of fluid levels marked in, for example, ounces, milliliters, or any other fluidic measurement. By comparing the fluid level seen through a translucent wall of the milk collection element shown in FIG. 3B with indicia 306, a user may ascertain the amount of milk contained within the milk collection element shown in FIG. 3B.

Figure 4:
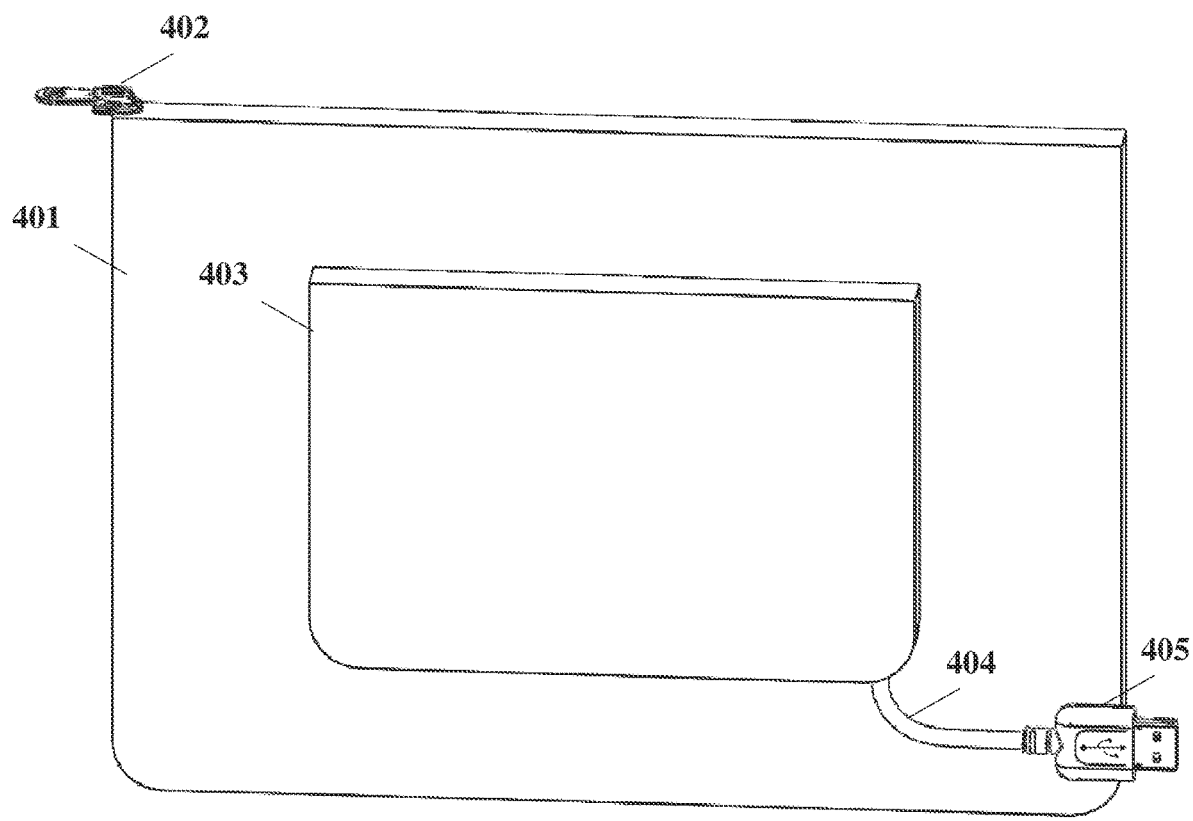
FIG. 4 illustrates a storage element of the smart breast pump system.

FIG. 4 illustrates a storage element of the smart breast pump system. The storage element in FIG. 4 may be implemented as a carrying case 401 to store various elements of the smart breast pump system when not in use. Carrying case 401 may take any form, including a purse, a clutch, and a bag. Carrying case 401 may be held closed by, for example, a zipper 402, as shown in FIG. 4, one or more buttons, one or more snaps, one or more magnetic attachments, or any other means for enclosing a carrying case known in the art. Carrying case 401 may be configured to contain one or more bottles of milk, such as bottle 304, shown in FIG. 3A.

Carrying case 401 may further include an additional compartment 403 configured to store electrical components of the smart breast pump system. For example, the sensor portion of milk capture and collection element 101 or external vacuum pump 103, each shown in FIG. 1, or a vacuum pump that is an integral component of milk capture and collection element 101 may be stored within additional compartment 403. Additional compartment 403 may include a charging cable 404 that may charge batteries associated with any of the electrical components of the milk capture and collection element 101 shown in FIG. 1 including mobile device 104. Charging cable may connect directly to the electrical components of milk capture and collection element 101, shown in FIG. 1, or, alternatively, may provide inductive charging technology to charge batteries using electrical induction. Charging cable 404 may be implemented with any type of connector known in the art. However, in a preferable embodiment, charging cable 404 includes a USB-A style adapter 405 that may be connected to a power source for charging batteries associated with any of the electrical components of the milk capture and collection element 101, shown in FIG. 1. Accordingly, adapter 405 may connect directly or indirectly to a source of power, such as a standard home electrical outlet, in order to charge the electrical components of the milk capture and collection element 101 shown in FIG. 1. Examples of indirect connections between adapter 405 and a source of power include connections to power adapters, transformers, or other devices meant to output power at a level appropriate for the electrical components of the milk capture and collection element 101 and the smart breast pump system disclosed herein.

Figure 5:
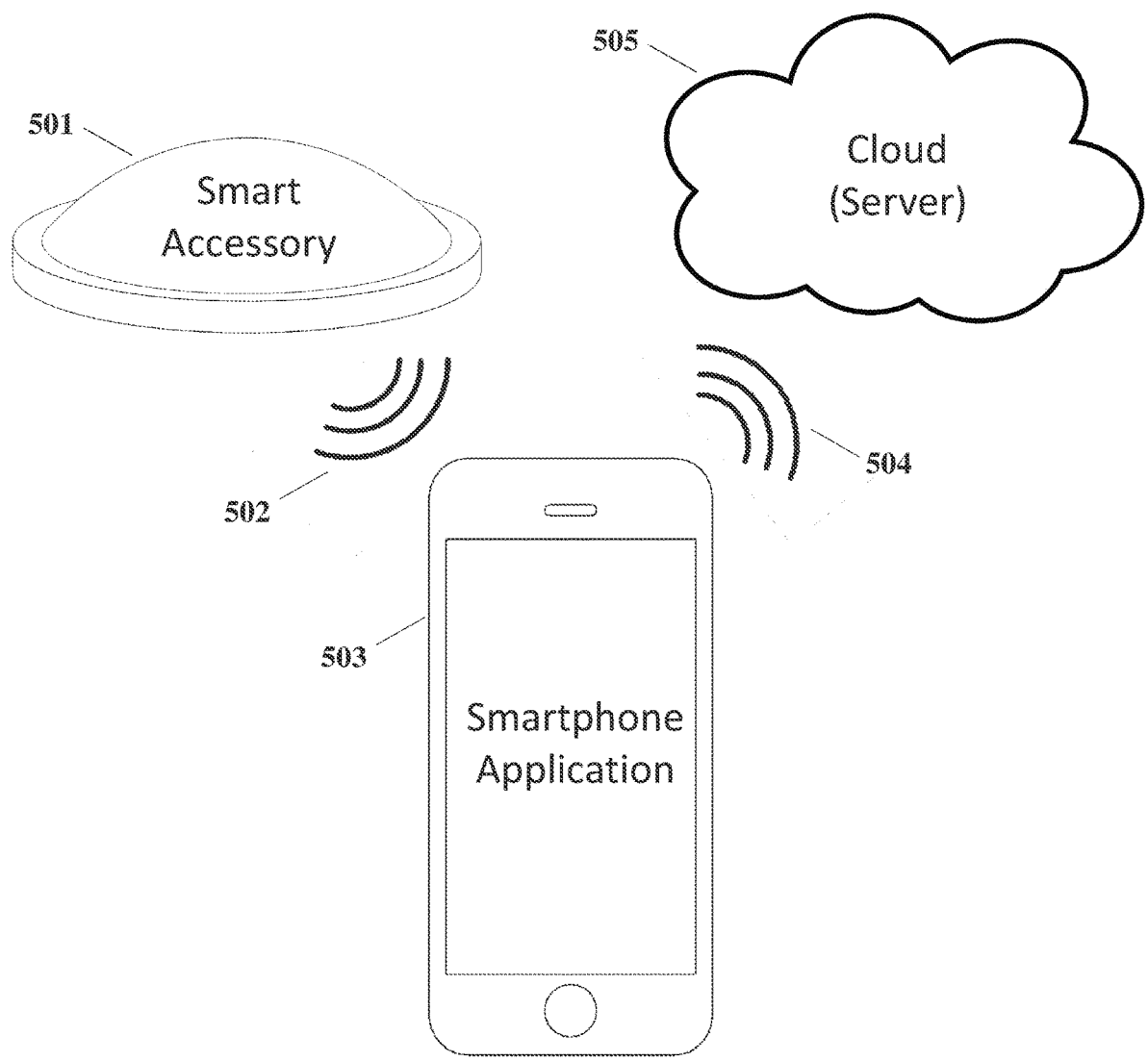
FIG. 5 illustrates an exemplary communication flow between various elements of the smart breast pump system.

FIG. 5 illustrates an exemplary communication flow between various elements of the smart breast pump system. A smart accessory 501, such as one or more sensors within the sensor portion of milk capture and collection element 101, shown in FIG. 1, may monitor milk expression in real time. For example, smart accessory 501 may monitor a flow rate of milk as it is expressed and/or a volume of milk contained within a milk collection portion of milk capture and collection element 101, shown in FIG. 1. As this information is collected by smart accessory 501, smart accessory 501 may transmit the information to mobile device 503 by a mobile device interface connection 502. In this configuration, mobile device interface connection 502 may be implemented using a short-range radio frequency technology, such as Bluetooth or Bluetooth low energy protocol. In many situations, it is likely that smart accessory 501 may be in relatively close proximity to mobile device 503 and therefore take advantage of short range communication protocols.

Mobile device 503, which is similar to mobile device 104 shown in FIG. 1, may implement an application that controls a user interface. Accordingly, information obtained from smart accessory 501 can be received by mobile device 503 and displayed on a user interface to provide a user with real-time feedback about a pumping session, including flow rate tracking, and the volume of milk contained within a milk collection portion of milk capture and collection element 101, shown in FIG. 1. The user interface device displayed on a display screen of mobile device 503 may provide any information, suggestion, or display disclosed herein with respect to other figures.

As shown in FIG. 5, mobile device 503 may transmit information derived from smart accessory 501 to a server 505 by means of a network interface connection 504. In this example, mobile device 503 implements a communication interface protocol suitable for transmission of data over distances greater than those implemented by mobile device interface connection 502. For example, Network interface connection 504 may be implemented using Wi-Fi, ZigBee, Z-Wave, RF4CE, Ethernet, telephone line, cellular channels, or others that operate in accordance with protocols defined in IEEE (Institute of Electrical and Electronics Engineers) 802.11, 801.11a, 801.11b, 801.11e, 802.11g, 802.11h, 802.11i, 802.11n, 802.16, 802.16d, 802.16e, or 802.16m using any network type including a wide-area network ("WAN"), a local-area network ("LAN"), a 2G network, a 3G network, a 4G network, a Worldwide Interoperability for Microwave Access (WiMAX) network, a Long Term Evolution (LTE) network, Code-Division Multiple Access (CDMA) network, Wideband CDMA (WCDMA) network, any type of satellite or cellular network, or any other appropriate protocol to facilitate communication between mobile device 503 and server 505.

Server 505 may be implemented as a cloud based server. For example, a cloud based server may be implemented as several servers connected in a fashion to perform server functions in a partitioned series of processing steps in order to produce faster results as a function of the combined processing power of many servers working together to accomplish a particular end. Further, data received by server 505 may be accessed via web browser by any allowed user. Accordingly, another parent, guardian, health care professional, doctor, counselor, or any other allowed person may monitor, download, and backup data in real time via the web browser.

The foregoing description has been presented for purposes of illustration. It is not exhaustive and does not limit the invention to the precise forms or embodiments disclosed. Modifications and adaptations will be apparent to those skilled in the art from consideration of the specification and practice of the disclosed embodiments. For example, components described herein may be removed and other components added without departing from the scope or spirit of the embodiments disclosed herein or the appended claims.

Other embodiments will be apparent to those skilled in the art from consideration of the specification and practice of the disclosure disclosed herein. It is intended that the specification and examples be considered as exemplary only, with a true scope and spirit of the invention being indicated by the following claims.

What is claimed is:
1. A smart breast pump system, comprising:
 a breast pump, including:
  a milk capture and collection element, including a sensor portion including at least one sensor to monitor the expression of breast milk, the sensor being disposed in the milk capture and collection element of the breast pump;
  a power source disposed within the breast pump;
  a milk collection portion including a bottle, the bottle including a valve which attaches to the bottle by enveloping a rim that protrudes radially from an opening of the bottle such that the valve mates with a stop disposed on an external surface of the bottle, wherein the stop extends radially outward from the external surface of the bottle beyond an outermost edge of the attached valve the valve including valve leaflets which, when installed, are disposed below the top edge of the bottle such that the valve leaflets are open to the bottle except when suction is applied to the valve leaflets,
wherein the at least one sensor is triggered to begin sensing a flow of breast milk into the milk collection portion in response to an installation of the milk collection portion on the milk capture and collection element of the breast pump,
wherein the sensor portion included in the milk capture and collection element of the breast pump includes wireless communication circuitry that transmits real-time breast milk expression information for breast milk into the milk collection portion; and
a suction pump, wirelessly receiving one or more control instructions based on real-time breast milk expression information, real-time suggestions provided to the user for controlling the pump, and user interaction based on the one or more real-time suggestions, the real-time breast milk expression information including at least real-time milk flow rate information.

2. The smart breast pump system of claim 1, further comprising: a cup portion.

3. The system of claim 1, wherein the breast milk expression information includes data representative of a non-real-time flow rate for breast milk expression.

4. The system of claim 1, wherein the breast milk expression information includes data representative of a volume of milk contained within the milk collection portion.

5. The system of claim 1, wherein the sensor receives one or more control instructions from a mobile device.

6. The system of claim 1, wherein the valve is removable.

7. The system of claim 2, wherein the cup portion comprises a cup configured to form an air tight seal between a breast and the cup upon application of vacuum pressure to the breast.

8. The system of claim 5, wherein the pump is external to the sensor portion and the milk collection portion.

9. The system of claim 5, wherein the pump included in the pump is integrated into the breast pump.

10. The system of claim 5, wherein the power source disposed within the breast pump is inductively charged.

11. The system of claim 8, wherein the pump is connected to the breast pump by pneumatic tubing.

12. The system of claim 6, wherein the valve leaflets comprise one or more pairs of valve leaflets.

13. The system of claim 12, wherein the one or more pairs of valve leaflets create a one-way valve through which milk is able to flow into the milk collection portion.

14. A smart breast pump system, comprising:
a breast pump, including:
a milk capture and collection element, including a sensor portion including at least one sensor to monitor the expression of breast milk, the sensor being disposed in the milk capture and collection element of the breast pump;
a power source disposed within the breast pump;
a milk collection portion including a bottle, the bottle including a valve which attaches to the bottle by enveloping a rim that protrudes radially from an opening of the bottle such that the valve mates with a stop disposed on an external surface of the bottle, wherein the stop extends radially outward from the external surface of the bottle beyond an outermost edge of the attached valve, the valve including valve leaflets which, when installed, are disposed below the top edge of the bottle such that the valve leaflets are open to the bottle except when suction is applied to the valve leaflets;
wherein the at least one sensor is triggered to begin sensing a flow of breast milk into the milk collection portion in response to an installation of the milk collection portion on the pump;
wherein the sensor portion included in the milk capture and collection element of the breast pump includes wireless communication circuitry that transmits real-time breast milk expression information for breast milk into the milk collection portion;
a mobile device, wirelessly receiving sensor data transmitted by the wireless communication circuitry included in the sensor portion of the milk capture and collection element of the breast pump, and controlling a suction pump, including a breast pump which applies vacuum pressure to the breast pump,
wherein based on the real-time breast milk expression information for breast milk into the milk collection portion which includes at least real-time milk flow rate information, the mobile device provides real-time suggestions for controlling the suction pump to a user, receives real time user interaction accepting or rejecting the suggestions for controlling the suction pump, and provides one or more control instructions to the suction pump based on the received real time user interaction; and
at least one server device, wirelessly receiving the sensor data from the at least one mobile device.

15. The system of claim 14, wherein the breast milk expression information is displayed in a user interface on a display screen of the mobile device.

16. The system of claim 14, wherein the breast milk expression information is accessible through the server device via a web browser.

17. The system of claim 14, wherein the mobile device transmits pump control information to the suction pump in real time.

18. The system of claim 14, wherein the mobile device wirelessly transmits one or more control instructions to the suction pump.

* * * * *